Oct. 19, 1965 F. W. ANDERSON Plant Pat. 2,564
PLUM TREE
Filed May 22, 1964
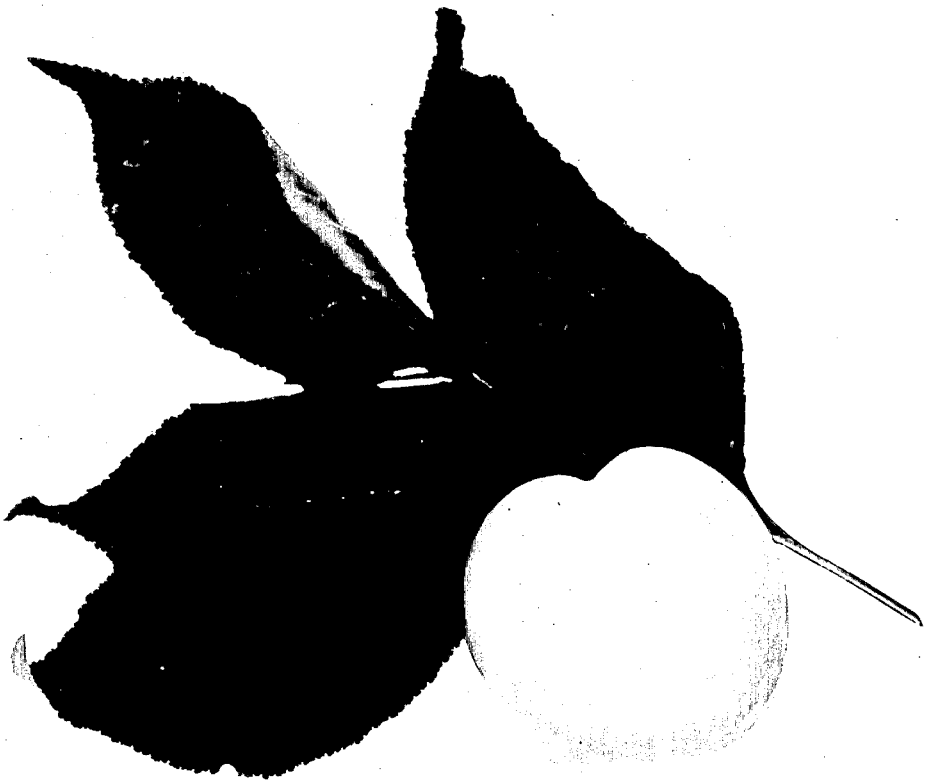
INVENTOR
*Frederic W. Anderson*
*Webster & Webster*
ATTYS.

United States Patent Office

Plant Pat. 2,564
Patented Oct. 19, 1965

2,564
PLUM TREE

Frederic W. Anderson, Merced, Calif., assignor to Peach & Willow Farms, Fresno, Calif., a corporation of California Filed May 22, 1964, Ser. No. 369,649
1 Claim. (Pit.—38)

This invention relates to a new and distinct variety of plum tree which is a sib of, and bears some resemblance in tree and fruit to, the Grand Rosa (United States Plant Patent No. 1,756). However, the present variety of plum tree is distinctively characterized, in comparison to the Grand Rosa, in the following respects:

The fruit, which requires heavier thinning, is slightly smaller in size; is of somewhat darker exterior color when ripe; ripens about one week later; and keeps better after picking; the latter feature assuring of a longer shelf life and which is of substantial commercial advantage.

The herein claimed variety of plum tree was originated by me in my experimental orchard located near Le Grand, Merced County, California, as follows:

Seeds from El Dorado (unpatented) plum tree growing adjacent Santa Rosa and Late Rosa (both unpatented) plum trees were gathered and planted in a nursery row; the present variety being one of the resultant seedlings, and which—at the time of bearing—evidenced the noted distinctive and desirable characteristics.

I subsequently asexually reproduced the variety by top-working on mature nectarine trees in my experimental orchard located as aforesaid, and all of such reproductions ran true to the parent in every respect.

The drawing comprises an illustration, by photographic reproduction in color, of a twig with leaves, a whole fruit, and another fruit cut in half with the halves disposed to expose the flesh.

Referring now more specifically to the pomological details of this new and distinct variety of plum tree, the following is an outline description thereof; all major color plate identifications being by reference to Maerz and Paul Dictionary of Color, except where common terms of color definition are employed.

Tree:
- *Size.*—Large to medium.
- *Vigor.*—Vigorous.
- *Growth.*—Spreading.
- *Density.*—Open.
- *Production.*—Very productive.
- *Bearing.*—Regular bearer.

Trunk: Size—medium.
Branches: Size—medium.
Leaves:
- *Size.*—Medium. Average length—2⅞". Average width—1 1/16".
- *Form.*—Oval.
- *Thickness.*—Medium
- *Margin.*—Crenate.
- *Petiole.*—Long to medium; medium thickness.
- *Glands.*—Average number—2 to 5. Small; positioned on blade.
- *Color.*—Top side—medium green (24–L–7). Under side—lighter green (23–L–6).

Flower Buds:
- *Size.*—Medium.
- *Length.*—Medium.

Flowers:
- *Blooming period.*—About with Late Rosa. Medium, as compared to other varieties.
- *Color.*—White.

Fruit:
- *Maturity when described.*—Eating ripe—September 10, 1963.
- *Date of first picking.*—August 20, 1963.
- *Date of last picking.*—September 8, 1963.
- *Size.*—Uniform; large to medium. Average diameter axially—2⅛". Average transversely in suture plane—2 1/16".
- *Form.*—Uniform; symmetrical; globose.
- *Suture.*—An inconspicuous line; shallow.
- *Ventral surface.*—Rounded slightly.
- *Cavity.*—Rounded. Average depth—9/16". Average breadth—⅝".
- *Base.*—Rounded.
- *Apex.*—Short; depressed.

Skin:
- *Thickness.*—Medium.
- *Texture.*—Medium.
- *Tendency to crack.*—Slight around stem end.
- *Down.*—Wanting.
- *Color.*—Yellow ground color (11–L–5) substantially overspread with red (6–L–6) shading darker in maturity.

Flesh:
- *Texture.*—Firm; fine; meaty.
- *Fibers.*—Few; tender.
- *Ripens.*—Evenly.
- *Flavor.*—Subacid; delicate.
- *Eating quality.*—Good.
- *Color.*—Yellow (11–L–4).

Stone:
- *Type.*—Free.
- *Size.*—Small. Average length—⅞". Average breadth—½". Average thickness—⅜".
- *Form.*—Oval.
- *Base.*—Straight.
- *Apex.*—Rounded.
- *Sides.*—Equal.
- *Ventral edge.*—Thin.
- *Dorsal edge.*—Full.
- *Tendency to split.*—None.
- *Color.*—Beige.

Use: Dessert. Market—local and long distance shipping.
Keeping quality: Very good.
Shipping quality: Very good.

The tree and its fruit herein described may vary in slight detail due to climatic and soil conditions under which the variety may be grown; the present description being of the variety as grown in the Central Valley of California.

The following is claimed:

A new and distinct variety of plum tree, substantially as illustrated and described, which is a regular and very productive bearer of yellow fleshed, freestone fruit having yellow skin substantially overspread with red; such fruit—in comparison to the Grand Rosa—requiring heavier thinning, being slightly smaller in size, ripening about one week later, having more red exterior color when ripe, and keeping better after picking.

No references cited.

ABRAHAM G. STONE, *Primary Examiner.*